United States Patent [19]

Traver et al.

[11] Patent Number: 5,556,629
[45] Date of Patent: Sep. 17, 1996

[54] METHOD OF PREPARING MICROEMULSIONS

[75] Inventors: Frank J. Traver, Troy; James H. Merrifield, Balston Spa, both of N.Y.

[73] Assignee: General Electric Company, Waterford, N.Y.

[21] Appl. No.: 153,324

[22] Filed: Nov. 15, 1993

Related U.S. Application Data

[63] Continuation-in-part of Ser. No. 120,616, Sep. 13, 1993, abandoned, which is a continuation-in-part of Ser. No. 759,275, Sep. 13, 1991, Pat. No. 5,244,598.

[51] Int. Cl.$^6$ .............................. A61K 7/00; B01J 13/00
[52] U.S. Cl. ..................... 424/401; 252/312; 252/314; 524/838
[58] Field of Search ..................... 252/312, 314; 106/287.11; 424/70.12, 70.122, 401; 524/838

[56] References Cited

U.S. PATENT DOCUMENTS

| | | | |
|---|---|---|---|
| 3,544,498 | 12/1970 | Holdstock et al. | 524/588 |
| 3,748,275 | 7/1973 | Bernheim et al. | 252/312 |
| 4,559,227 | 12/1985 | Chandra et al. | 424/70.122 |
| 4,595,512 | 6/1986 | Tellier et al. | 252/312 X |
| 4,620,878 | 11/1986 | Gee | 106/287.15 |
| 4,631,273 | 12/1986 | Blehm et al. | 252/312 X |
| 4,705,704 | 11/1987 | Lane et al. | 427/389.9 |
| 4,733,677 | 3/1988 | Gee et al. | 132/7 |
| 4,743,648 | 5/1988 | Hill et al. | 106/287.12 X |
| 4,785,067 | 11/1988 | Brumbill | 528/26 |
| 4,797,272 | 1/1989 | Linn et al. | 425/59 |
| 4,824,877 | 4/1989 | Glover et al. | 523/221 |
| 4,842,766 | 6/1989 | Blehm et al. | 252/309 |
| 4,935,464 | 6/1990 | Ona et al. | 524/838 X |
| 4,999,398 | 3/1991 | Graiver et al. | 524/837 |
| 5,057,572 | 10/1991 | Chrobaczek et al. | 524/588 |
| 5,064,694 | 11/1991 | Gee | 252/312 X |
| 5,073,593 | 12/1991 | Ozaki et al. | 524/838 X |
| 5,077,040 | 12/1991 | Bergmann et al. | 424/70.122 |
| 5,132,443 | 7/1992 | Traver et al. | 556/425 |
| 5,244,598 | 9/1993 | Merrifield et al. | 252/314 |

FOREIGN PATENT DOCUMENTS

| 2024797 | 3/1991 | Canada. |
| 0417047A2 | 9/1990 | European Pat. Off.. |
| 0442098A2 | 12/1990 | European Pat. Off.. |
| WO88/08436 | 4/1988 | WIPO. |

OTHER PUBLICATIONS

European Search Report, Dec. 22, 1992.

*Primary Examiner*—Richard D. Lovering
*Attorney, Agent, or Firm*—Kenneth S. Wheelock

[57] ABSTRACT

A method for polymerizing polysilicone precursors via emulsion polymerization to yield transparent oil in water polysilicone microemulsions suitable for personal care applications is disclosed.

20 Claims, No Drawings

METHOD OF PREPARING MICROEMULSIONS

CROSS-REFERENCE TO RELATED APPLICATION

The instant application is a continuation-in-part of U.S. Ser. No. 08/120,616 filed Sep. 13, 1993 and now abandoned, which is a continuation-in-part of U.S. Ser. No. 07/759,275, filed Sep. 13, 1991 now allowed and issued as U.S. Pat. No. 5,244,598 on Sep. 14, 1993.

FIELD OF THE INVENTION

The instant invention comprises an emulsion polymerization process for making transparent oil in water microemulsions of polyorganosiloxanes.

BACKGROUND OF THE INVENTION

The instant invention is related to a method for making microemulsions. More particularly the instant invention is related to a method of making microemulsions having an average particle size of from about 0.001 microns to about 0.05 microns.

Microemulsions containing silicone fluids have been found to be useful in a variety of personal care products such as hair conditioners and other cosmetic formulations. As defined herein, the term "microemulsions" refers to transparent, mechanically and thermally stable systems comprising small droplets having a mean or average particle diameter usually not more than 0.05 microns in diameter, preferably not more than 0.040 microns in diameter and most preferably not more than 0.025 microns in diameter. The small size of the droplets imparts a high degree of transparency to the emulsion. Cosmetic formulations containing microemulsions possess improved aesthetic values as well as improved physical properties.

The use of microemulsions in cosmetic applications is known in the art, see for example U.S. Pat. Nos. 4,797,272 (Linnet al.) and 4,620,878 (Gee). U.S. Pat. No. 4,797,272 to Linnet al. discloses water-in-oil microemulsion compositions having a mean droplet size ranging from about 0.001 microns to about 0.200 microns and containing moisturizers or sunscreens, surfactants, oils (e.g. cyclic dimethyl polysiloxanes), and skin humectants. U.S. Pat. No. 4,620,878 to Gee discloses a polyorganosiloxane emulsion that contains a polyorganosiloxane containing at least one polar radical such as an amino radical attached to the silicon of the siloxane by Si—s C or Si—O—C bonds or at least one silanol radical and a surfactant that is insoluble in the polyorganosiloxane. The emulsion prepared by Gee has an average particle size of less than 0.14 microns and can be prepared by forming a translucent oil concentrate by mixing the polyorganosiloxane, at least one surfactant, an water and then forming a polyorganosiloxane emulsion of the oil-in-water type by rapidly dispersing the translucent oil concentrate in water.

It continues to be desirable to provide alternative or improved methods for preparing microemulsions of small average particle size. The instant invention arises from the discovery that the average particle size of silicone microemulsions can be reduced by preparing silicone microemulsions using the techniques of emulsion polymerization. This discovery may be broadened to include other microemulsions achievable by emulsion polymerization, such as the formation of aqueous microemulsions of polyacrylates or latexes.

SUMMARY OF THE INVENTION

In one aspect, the instant invention provides a method of preparing a transparent polyorganosiloxane microemulsion having a mean particle size of from about 0.001 to about 0.050 microns, preferably from about 0.010 to about 0.030 microns, and most preferably from about 0.010 to about 0.025 microns, comprising the steps of:

(A) forming an emulsion polymerization precursor mixture by blending:
  (1) 100 parts of a polyorganosiloxane comprising:
    (a) $R_a Q_b SiO_{(4-a-b)/2}$ units; and
    (b) $R_c SiO_{(4-c)/2}$ units;
  wherein the molar ratio of $R_a Q_b SiO_{(4-a-b)/2}$ units to $R_c SiO_{(4-c)/2}$ units ranges from about 1:2 to about 1:65 "a" assumes values ranging from about 1 to about 2, "b" assumes values ranging from about 1 to about 3, "a"+"b" is less than or equal to 3, "c" is a number in the range of from about 1 to about 3, R is a hydrocarbon or hydrocarbon radical having from 1 to about 6 carbon atoms, Q is a polar radical having the general formula —$R^1$NHZ, wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals containing from 1 to 4 carbon atoms, and —$CH_2CH_2NH_2$ radicals; and
  (2) from about 10 to 60 parts by weight per 100 parts of A(1) of at least one surfactant, said surfactant being a polyethylene glycol type surfactant, wherein at least one of the surfactants is insoluble in the polyorganosiloxane;
  (3) water in the amount of from about 100 to about 300 parts by weight based on the weight of the oil and surfactant mixture;
  (4) an alkali metal hydroxide selected from the group consisting of lithium, sodium, potassium, rubidium, and cesium hydroxides in the amount of from about 1 to about 20 parts by weight per weight of A(1);

(B) homogenizing the blend under a pressure ranging from about 1,000 to 15,000 psig;

(C) re-homogenizing the blend under the conditions in step(B);

(D) heating the blend to a temperature ranging from about 50 to about 150 C.;

(E) polymerizing the blend for a period of time ranging from about one to about five hours at a temperature ranging from about 50 to about 150 C until the blend reaches a solids content ranging from about 15 weight percent to about 50 weight percent (applicants note that steps (D) and (E) are usually simultaneous); and (F) terminating the polymerization by buffering the reaction blend being polymerized to a pH ranging from about 3 to about 7 using a weakly acidic carboxylic acid.

Other aspects of the invention are microemulsions of polydimethylsiloxane, polymethylmethacrylates and the like, cosmetic formulations involving the microemulsions of the aminofunctional polyorganosiloxane microemulsions and the polyorganosiloxanes, coating formulations and pigment carrier formulations involving the polyacrylate microemulsions and the like.

DETAILED DESCRIPTION OF THE INVENTION

The instant invention is based upon the discovery that polysiloxane precursors may be polymerized in an emulsion polymerization to yield polyorganosiloxane emulsions having a small particle size directly instead of first having to prepare the polymer and then emulsify same. Such microemulsions are generally transparent. By transparent applicants mean the absence of turbidity or haze wherein haze is defined by an ASTM test, specifically ASTM test number D871 using turbidity suspension standards and wherein said haze or turbidity is below an upper limit of about 150. At higher levels of the haze number the microemulsions of the present invention gradually change from transparent to translucent. The haze numbers of the microemulsions of the present invention range from 0 to about 150, more preferably from about 0 to about 80 and most preferably from 0 to about 50. The turbidity suspension standards used in the ASTM test D871 are available from Hellige Incorporated of Garden City, N.Y. Applicants note that pure distilled water is 0 on the haze scale.

Polyorganosiloxane microemulsions prepared by the method of the instant invention have a mean particle size of from about 0.005 to about 0.050 microns, preferably from about 0.010 to about 0.030 microns, and most preferably from about 0.010 to about 0.025 microns. Generally haze and average particle size correlate with one another but they are also affected by the relative amounts of the two major components of the emulsion, the silicone oil and the water. Thus while at a constant oil to water ratio the haze and average particle size might correlate, haze by itself is not both a necessary and sufficient criterion to be an indicator of average particle size in a microemulsion unless other constraints are specified.

In step (A) of the method of the instant invention an oil surfactant mixture is prepared by blending:

(1) 100 parts of a polyorganosiloxane optionally having an amino content of from about 0.6 to about 3.0 milliequivalents per gram and comprising:
 (a) $R_aQ_bSiO_{(4-a-b)/2}$ units; and
 (b) $R_cSiO_{(4-c)/2}$ units.

In the formulas above R is a hydrocarbon or hydrocarbon radical having from 1 to about 6 carbon atoms, Q is a polar radical having the general formula —$R^1$NHZ, wherein $R^1$ is a divalent linking group comprised of carbon and hydrogen atoms; carbon, hydrogen and oxygen, atoms, or carbon, hydrogen and sulfur atoms; and Z is a radical selected from the group consisting of hydrogen atoms, alkyl radicals containing from 1 to 4 carbon atoms, and —$CH_2CH_2NH_2$ radicals; and (2) from about 10 to 60 parts by weight per part 100 parts of A(1) of at least one surfactant, wherein at least one of the surfactants is insoluble in the polyorganosiloxane; (3) water in the amount of from about 100 to about 300 parts by weight based on the weight of the oil and surfactant mixture; (4) an alkali metal hydroxide selected from the group consisting of lithium, sodium, potassium, rubidium, and cesium hydroxides in the amount of from about 1 to about 20 parts by weight per weight of A(1). In step(B) of the instant invention, the blend is homogenized the blend under a pressure ranging from about 1,000 to 15,000 psig. In step (C) of the instant invention the blend is re-homogenized under the conditions in step(B). In step (D) of the instant invention the blend is heated to a temperature ranging from about 50° to about 150° C. Generally step (D) is carried out at temperatures ranging from 85° to 95° C. Higher temperatures for step (D) will necessitate the use of higher pressures in order to prevent the loss of reactants by distillation. In step (E) of the instant invention, the blend is polymerized for a period of time ranging from about one to about five hours at a temperature ranging from about 50° to about 150° C. until the blend reaches a solids content ranging from about 15 weight percent to about 50 weight percent. In step (F) of the instant invention the polymerization of the blend is terminated by buffering the reaction blend being polymerized to a pH ranging from about 3 to about 7 using a weakly acidic carboxylic acid.

Non-limiting examples of radicals represented by R include alkyl radicals such as methyl, ethyl, propyl, isopropyl, butyl, isobutyl, amyl, isoamyl, hexyl, isohexyl, and the like; alkenyl radicals such as vinyl, halo vinyl, alkyl vinyl, allyl, haloalkyl, alkylallyl, cycloalkyl radicals such as cyclobutyl, cyclopentyl, cyclohexyl and the like, phenyl radicals, benzylradicals, halohydrocarbon radicals such as 3-chloropropyl, 4-bromobutyl, 3,3,3-trifluoropropyl, chlorocyclohexyl, bromophenyl, chlorophenyl and the like, and sulfur containing radicals such as mercaptoethyl, mercaptopropyl, mercaptohexyl, mercaptophenyl and the like.

Preferably R is an alkyl radical containing from 1 to about 6 carbon atoms. Most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$, —$(CH_2)_3CC(O)OCH_2CH_2$—, —$C_6H_4C_6H_4$—, —$C_6H_4CH_2C_6H_4$—, and —$(CH_2)_3C(O)SCH_2CH_2$—.

Z is most preferably a —$CH_2CH_2NH_2$ radical.

Q is most preferably an amine functional polar radical having the formula —$CH_2CH_2CH_2NHCH_2CH_2NH_2$.

In the formulas for the units 9a) and (b), "a" assumes values ranging from about 1 to about 2, "b" assumes values ranging from about 1 to about 3, "a"+"b" is less than or equal to 3, and "c" is a number in the range of from about 1 to about 3. The molar ratio of $R_aQ_bSiO_{(4-a-b)/2}$ units to $R_cSiO_{(4-c)/2}$ units ranges from about 1:2 to about 1:65, preferably from about 1:5 to about 1:65, and most preferably from about 1:15 to about 1:20.

When it is preferred to use amino functional silicone fluids (A)(1) in the instant invention the preferred fluids have the formula:

wherein x is a number in the range of from 1 to about 20 preferably from about I to 10 and most preferably about 8, and y is a number in the range from about 20 to about 800 preferably from about 100 to about 500 and most preferably about 275.

(A)(2) contains at least one surfactant, wherein at least one of the surfactants is insoluble in the silicone of (A)(1), said surfactant hereinafter referred to as the primary surfactant. Other optional surfactants are referred to as secondary surfactants.

The surfactant or blend of surfactants has a hydrophiliclipophilic balance value of from about 10 to about 16, preferably from about 12 to about 16, and most preferably from about 13 to about 14.

The primary surfactant may be cationic, anionic, nonionic or amphoteric in nature. Examples of such surfactants are disclosed in U.S. Pat. No. 4,620,878 to Gee which is hereby incorporated by reference. Generally, nonionic surfactants are preferred for use in the instant invention.

Surfactants useful as the primary surfactant in the instant invention include the sorbitan esters of fatty acids having 10 to 22 carbon atoms; polyoxyethylene sorbitan esters of $C_{10}$ to $C_{22}$ fatty acids having up to 95% ethylene oxide; polyoxyethylene sorbitol esters of $C_{10}$ to $C_{22}$ fatty acids, polyoxyethylene derivatives of fatty phenols having 6 to 20 carbon atoms up to 95% ethylene oxide; fatty amino and amido betaines having 10 to 22 carbon atoms, and polyethylene condensates of $C_{10}$ to $C_{22}$ fatty acids or fatty alcohols having up to 95% ethylene oxide.

Preferred primary surfactants for the practice of the instant invention include, but are not limited to, the octylphenoxy polyethoxy ethanols, which are nonionic surfactants possessing varying amounts of ethylene oxide units and are available from Union Carbide Corporation under the general Triton® trade name; trimethylnonyl polyethylene glycol ethers and polyethylene glycol ethers of linear 11–15 carbon atoms containing alcohols, available form Union Carbide Corporation under the general trade name Tergitol®; the nonionic ethoxylated tridecyl ethers, available from Emery Industries under the trade name Trycol®; polyethoxylated quaternary ammonium salts and ethylene oxide condensation products of fatty amines available from Armak Company under the general trade names Ethoquad® and Ethomeen®, respectively, and alkoxylated siloxane surfactants containing ethylene oxide and/or propylene oxide groups. The surfactants listed herein above may be obtained from other suppliers under different trade names.

The preferred surfactants for use as the primary surfactant of the instant invention are the trimethylnonyl polyethylene glycol ethers and polyethylene glycol ethers of linear 11–15 carbon atom containing alcohols, available from Union Carbide Corporation under the trade name Tergitol®. A preferred surfactant for use as the primary surfactant of the instant invention is a trimethylnonyl polyethylene glycol ether. The most preferred primary surfactant is N,N,N',N', N'-pentamethyl-N-tallow-1,3-diammonium chloride.

The optional secondary surfactants may artionic, cationic, nonionic, or amphoteric and may either be soluble or insoluble in the amino functional silicone of (A)(1). Nonionic surfactants are preferred as the secondary surfactant of the instant invention. Non-limiting examples of surfactants that are soluble in the amino functional silicone include the alkyl phenol ethoxylates.

Preferably, the optional secondary surfactant used in this invention is also insoluble in the silicone of (A)(1). The preferred surfactant for use as the secondary surfactant in the instant invention is a 70% aqueous solution of octylphenoxy polyethoxy (40) ethanol.

Preferably (A)(2) is a mixture of two nonionic surfactants, trimethyl nonyl polyethylene glycol ether (primary surfactant) and 70% aqueous solution of octylphenoxy polyethoxy (40) ethanol (secondary surfactant) being preferred, at a primary surfactant to secondary surfactant weight ratio of from about 1:2 to about 5:1, preferably from about 1:1 to about 3:1, and most preferably from about 9:2 to about 11:5.

The amount of optional (A)(2) is in the range of from about 10 to about 60, preferably from about 20 to about 40, and most preferably from about 25 to about 35, parts by weight per 100 parts by weight of (A)(1).

In step (B) of the instant invention, the blend of silicones, surfactants and water is homogenized under a pressure ranging from about 1,000 to 15,000 psig in a homogenizer or other suitable mixing equipment. The length of time necessary to form a homogeneous mixture or emulsion in this step will depend on mixing equipment parameters and can be determined by those skilled in the art without undue experimentation.

In step (C) of the instant invention, the blend is re-homogenized under the conditions in step (B).

In step (D) of the instant invention, the blend is heated to a temperature ranging from about 50° to about 150° C., more preferably from about 750° to about 125° C., and most preferably from about 85° to about 95° C.

In step (E) of the instant invention the blend is polymerized for a period of time ranging from about one to about five hours at a temperature ranging from about 50° to about 150° C. until the blend reaches a solids content ranging from about 15 weight percent to about 50 weight percent, more preferably from about 20 weight percent to about 40 weight percent, and most preferably from about 25 weight percent to about 35 weight percent.

In step (F) of the instant invention, the polymerization is terminated by modifying the pH of the reaction medium to a pH ranging from about 3 to about 7, preferably a pH ranging from about 4.5 to about 6, and most preferably from about 4.5 to about 5, using a weakly acidic carboxylic acid having for or fewer carbon atoms, more preferably from 2 to 4 carbon atoms, and most preferably being acetic acid, or alternatively using a mineral acid selected from the group consisting of HCl, HBr, HI, $H_2SO_4$, and $HNO_3$. Of the mineral acids, it is preferred to use HCl.

In order to change the pH of the reaction medium, it is necessary to consider the quantity of amino functional silicone or silicone present in the reaction mixture. The amount of acid needed to provide such pH values will depend on the amount of the amino functional silicone or silicone fluid (A)(1) and the amino content of the amino functional silicone fluid. For example, with the amino functional silicone fluid having an amino content of 0.6 milliequivalents per gram, the amount of acid sufficient to provide a pH within the desired range will be approximately 2.5 parts per weight per 100 parts per weight of the amino functional silicone fluid. With an amino functional silicone fluid having an amino content of 3.0 milliequivalents per gram, the weight of acid will be about 12.5 parts per weight per 100 parts per weight of the fluid. While the weights of acid necessary to achieve a given pH may vary depending on the molecular and equivalent weights of the acid chosen to control the pH, control of pH to the desired value is the primary purpose of the acid addition.

EXPERIMENTAL

EXAMPLE 1

A blend was prepared from;

64 gm of a low molecular weight aminofunctional silicone having aminopropyl end groups, 134 gm of octamethylcyclotetrasiloxane (tetraruer), 100 gm of TERGITOL® 15-S-20, 22 gm of N,N,N',N',N'-pentamethyl-N-tallow-1,3-diammonium chloride, 5.9 gm potassium hydroxide, and 700 gm of water.

The blend was homogenized in a Gaulin homogenizer using two passes at 10,000 psig.

The homogenized blend was heated at 89° to 92° C. for three hours to polymerize the blend to a solids level of 26.3 weight percent solids. In appearance the emulsion had a very fine apparent particle size. Measured on a Nicomp 370 analyzer, the mean particle size was found to 20.7 nm. The polymerization was stopped and the emulsion was buffered by the addition of 15.0 gm of acetic acid. After buffering the particle size was redetermined and the mean particle size was found to be 11.2 nm. The emulsion was clear with a slight yellow color.

EXAMPLE 2

A blend was prepared from:

23 gm of tetramer designated 81365, 170 gm of tetraruer, 20 gm of 50% aqueous benzenethonium chloride (a cationic surfactant), 5.0 gm potassium hydroxide, 70 gm of a polyoxyethylene cetyl ether having 20 $CH_2CH_2O$ units and sold as Brij58® by ICI Specialty Chemicals, 7 gm of decamethylpentasiloxane (pentamer), 72 gm of phenoxy polyoxyethylene glycol sold as Macol NP-20°® by PPG Industries, and 640 gm of water.

The blend was homogenized in a Gaulin homogenizer using two passes at 8,000 psig.

The homogenized blend was heated at 91° to 92° C. for three hours to polymerize the blend to a solids level of 36.5 weight percent solids. In appearance the emulsion had a very fine apparent particle size. The polymerization was stopped and the emulsion was buffered by the addition of 5.0 gm of acetic acid. After buffering the particle size was determined and the mean particle size was found to be 35.1 nm. The emulsion was transparent but slightly turbid.

Having described in invention, we claim:

1. A transparent oil-in-water silcone-containing microemulsion, prepared by the technique of emulsion polymerization comprising the steps of:
   a) blending
      1) a polyorganosiloxane optionally having an amino content of from about 0.6 to about 3.0 milliequivalents per gram and comprising:
         (i) $R_aQ_bSiO_{(4-a-b)/2}$ units; and
         (ii) $R_cSiO_{(4-c)/2}$ units
      where R is a hydrocarbon or hydrocarbon radical having from 1 to about 6 carbon atoms, Q is a polar radical having the general formula $R^1NHZ$, Wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals containing from 1 to 4 carbon atoms, and $-CH_2CH_2NH_2$ radicals wherein a assumes values ranging from about 1 to about 2, assumes values ranging from about 1 to about 3, a+b is less than or equal to 3, and c ranges from about 1 to about 3;
      (2) from about 10 to 60 parts by weight per part 100 parts of A(1) of at least one surfactant, said surfactant being a polyethylene glycol type surfactant, wherein at least one of the surfactants is insoluble in the polyorganosiloxasne;
      (3) water in the amount of from about 100 to about 300 parts by weight based on the weight of the oil and surfactant mixture;
      (4) an alkali metal hydroxide selected from the group consisting of lithium, sodium, potassium, rubidium, and cesium hydroxides in the amount of from about 1 to about 20 parts by weight per weight of A(1);
   b) homogenizing the blend of a step a) at a pressure ranging from 1,000 to 15,000 psig;
   c) re-homogenizing the blend of step b) under the conditions of step b);
   d) heating the blend at a temperature ranging from about 50° to about 150° C. for a period of time ranging from about one to about ten hours until the solids content of the blend ranges from about ten weight percent to about fifty weight percent; and
   e) buffering the blend to a pH ranging from about 3 to about 7 by adding an effective amount of an acid selected from the group consisting of a weakly acidic carboxylic acids having four or fewer carbon atoms; whereby the average particle size of the emulsion ranges from about 0.001 to about 0.050 microns, wherein the haze of said microemulsion as defined by ASTM test D871 is below about 150.

2. The microemulsion of claim 1 wherein the average particle size ranges from 0001 to about 0.040 microns.

3. The microemulsion of claim 1 wherein the average particle size ranges from 0.001 to about 0.025 microns.

4. A method for preparing transparent oil-in-water silicone-containing microemulsions comprising the steps of:
   a) blending
      1) a polyorganosiloxane optionally having an amino content of from about 0.6 to about 3.0 milliequivalents per gram and comprising:
         (i) $R_aQ_bSiO_{(4-a-b)/2}$ units; and
         (ii) $R_cSiO_{(4-c)/2}$ units
      wherein R is a hydrocarbon or hydrocarbon radical having from 1 to about 6 carbon atoms, Q is a polar radical having the general formula $-R^1NHZ$, wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals containing from 1 to 4 carbon atoms, and $-CH_2CH_2NH_2$ radicals, wherein a assumes values ranging from about 1 to about 2, b assumes values ranging from about 1 to about 3, a+b is less than or equal to 3, and c ranges from about 1 to about 3;
      (2) from about 10 to 60 parts by weight per part 100 parts of A(1) of at least one surfactant, said surfactant being a polyethylene glycol type surfactant, wherein at least one of the surfactants is insoluble in the polyorganosiloxane;
      (3) water in the amount of from about 100 to about 300 parts by weight based on the weight of the oil and surfactant mixture;
      (4) an alkali metal hydroxide selected from the group consisting of lithium, sodium, potassium, rubidium, and cesium hydroxides in the amount of from about 1 to about 20 parts by weight per weight of A(1);
   b) homogenizing the blend of step a) at a pressure ranging from 1,000 to 15,000 psig;
   c) re-homogenizing the blend of step b) under the conditions of step b);
   d) heating the blend at a temperature ranging from about 50 to about 150° C. for a period of time ranging from about one to about ten hours until the solids content of the blend ranges from about ten weight percent to about fifty weight percent; and
   e) buffering the blend to a pH ranging from about 3 to about 7 by adding an effective amount of an acid selected from the group consisting of a weakly acidic carboxylic acids having four or fewer carbon atoms; whereby the average particle size of the emulsion ranges from about 0.001 to about 0.050 microns, wherein the haze of said microemulsion as defined by ASTM test D871 is below about 150.

5. The method of claim 4 wherein the average particle size ranges from 0.001 to about 0.040 microns.

6. The method of claim 4 wherein the average particle size ranges from 0.001 to about 0.025 microns.

7. A transparent oil-in-water silicone-containing microemulsion, prepared by the technique of emulsion polymerization comprising the steps of:
a) blending
1) a polyorganosiloxane optionally having an amino content of from about 0.6 to about 3.0 milliequivalents per gram and comprising:
(i) $R_aQ_bSiO_{(4-a-b)/2}$ units; and
(ii) $R_cSiO_{(4-c)/2}$ units
wherein R is a hydrocarbon or hydrocarbon radical having from 1 to about 6 carbon atoms, Q is a polar radical having the general formula —$R^1NHZ$, wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals containing from 1 to 4 carbon atoms, and —$CH_2CH_2NH_2$ radicals, wherein a assumes values ranging from about 1 to about 2, b assumes values ranging from about 1 to about 3, a+b is less than or equal to 3, and c ranges from about 1 to about 3;
(2) from about 10 to 60 parts by weight per part 100 parts of A(1) of at least one surfactant, said surfactant being a polyethylene glycol type surfactant, wherein at least one of the surfactants is insoluble in the polyorganosiloxane;
(3) water in the amount of from about 100 to about 300 parts by weight based on the weight of the oil and surfactant mixture;
(4) an alkali metal hydroxide selected from the group consisting of lithium, sodium, potassium, rubidium, and cesium hydroxides in the amount of from about 1 to about 20 parts by weight per weight of A(1);
b) homogenizing the blend of step a) at a pressure ranging from 1,000 to 15,000 psig;
c) re-homogenizing the blend of step b) under the conditions of step b);
d) heating the blend at a temperature ranging from about 50 to about 150° C. for a period of time ranging from about one to about ten hours until the solids content of the blend ranges from about ten weight percent to about fifty weight percent; and
e) buffering the blend to a pH ranging from about 3 to about 7 by adding an effective amount of an acid selected from the group consisting of hydrochloric, hydrobromic, sulfuric, and phosphoric acids; whereby the average particle size of the emulsion ranges from about 0.001 to about 0.050 microns, wherein the haze of said microemulsion as defined by ASTM test D871 is below about 150.

8. The microemulsion of claim 7 wherein the average particle size ranges from 0.001 to about 0.040 microns.

9. The microemulsion of claim 7 wherein the average particle size ranges from 0.001 to about 0.025 microns.

10. A method for preparing transparent oil-in-water silicone-containing microemulsions comprising the steps of:
a) blending
1) a polyorganosiloxane optionally having an amino content of from about 0.6 to about 3.0 milliequivalents per gram and comprising:
(i) $R_aQ_bSiO_{(4-a-b)/2}$ units; and
(ii) $R_cSiO_{(4-c)/2}$ units
wherein R is a hydrocarbon or hydrocarbon radical having from 1 to about 6 carbon atoms, Q is a polar radical having the general formula —$R^1NHZ$, wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals containing from 1 to 4 carbon atoms, and —$CH_2CH_2NH_2$ radicals, wherein a assumes values ranging from about 1 to about 2, b assumes values ranging from about 1 to about 3, a+b is less than or equal to 3, and c ranges from about 1 to about 3;
(2) from about 10 to 60 parts by weight per part 100 parts of A(1) of at least one surfactant, said surfactant being a polyethylene glycol type surfactant, wherein at least one of the surfactants is insoluble in the polyorganosiloxane;
(3) water in the amount of from about 100 to about 300 parts by weight based on the weight of the oil and surfactant mixture;
(4) an alkali metal hydroxide selected from the group consisting of lithium, sodium, potassium, rubidium, and cesium hydroxides in the amount of from about 1 to about 20 parts by weight per weight of A(1);
b) homogenizing the blend of step a) at a pressure ranging from 1,000 to 15,000 psig;
c) re-homogenizing the blend of step b) under the conditions of step b);
d) heating the blend at a temperature ranging from about 50 to about 150° C. for a period of time ranging from about one to about ten hours until the solids content of the blend ranges from about ten weight percent to about fifty weight percent; and
e) buffering the blend to a pH ranging from about 3 to about 7 by adding an effective amount of an acid selected from the group consisting of hydrochloric, hydrobromic, sulfuric and phosphoric acid; whereby the average particle size of the emulsion ranges from about 0,001 to about 0,050 microns, wherein the haze of said microemulsion as defined by ASTM test D871 is below about 150.

11. The method of claim 10 wherein the average particle size ranges from 0.001 to about 0.040 microns.

12. The method of claim 10 wherein the average particle size ranges from 0.001 to about 0.025 microns.

13. Cosmetic formulations for personal care products comprising the microemulsion of claim 1.

14. Cosmetic formulations for personal care products comprising microemulsions produced by the method of claim 4.

15. Cosmetic formulations for personal care products comprising the microemulsion of claim 7.

16. Cosmetic formulations for personal care products comprising microemulsions produced by the method of claim 10.

17. Cosmetic formulations for personal care products comprising the microemulsion of claim 2.

18. Cosmetic formulations for personal care products comprising microemulsions produced by the method of claim 5.

19. Cosmetic formulations for personal care products comprising the microemulsion of claim 8.

20. Cosmetic formulations for personal care products comprising microemulsions produced by the method of claim 11.

* * * * *

UNITED STATES PATENT AND TRADEMARK OFFICE
CERTIFICATE OF CORRECTION

PATENT NO. : 5,556,629

DATED : September 17, 1996

INVENTOR(S) : Frank J. Traver, et. al.

It is certified that error appears in the above-indentified patent and that said Letters Patent is hereby corrected as shown below:

Column 7, claim 1, line 43, after , and before the word assumes there should a b. Also claim 1, line 50 polyorganosiloxasne should be-- polyorganosiloxane--.

Signed and Sealed this

Eleventh Day of February, 1997

Attest:

BRUCE LEHMAN

Attesting Officer  Commissioner of Patents and Trademarks